(12) United States Patent
Millar

(10) Patent No.: US 6,416,651 B1
(45) Date of Patent: Jul. 9, 2002

(54) MULTI-ELECTRODE COMPOSITION MEASURING DEVICE AND METHOD

(75) Inventor: Ord Millar, Pierrefonds (CA)

(73) Assignee: Honeywell Measurex, Morristown, NJ (US)

( * ) Notice: Subject to any disclaimer, the term of this patent is extended or adjusted under 35 U.S.C. 154(b) by 0 days.

(21) Appl. No.: 09/258,550

(22) Filed: Feb. 26, 1999

(51) Int. Cl.⁷ .......................... G01N 27/48; G01N 27/49
(52) U.S. Cl. ...................... 205/775; 205/789; 204/400; 204/406; 204/412
(58) Field of Search ................................ 204/400, 412, 204/406, 409; 205/775, 781.5, 789, 789.5, 793.5, 794.5

(56) References Cited

U.S. PATENT DOCUMENTS

| | | | | |
|---|---|---|---|---|
| 3,676,321 A | * | 7/1972 | Cummings et al. | 204/412 |
| 3,922,205 A | * | 11/1975 | McLean et al. | 204/413 |
| 4,500,391 A | * | 2/1985 | Schmidt et al. | 204/406 |
| 4,883,057 A | * | 11/1989 | Broderick | 128/631 |
| 4,900,405 A | * | 2/1990 | Otagawa et al. | 204/412 |
| 4,937,038 A | * | 6/1990 | Sakai et al. | 376/245 |
| 5,223,117 A | * | 6/1993 | Wrighton et al. | 204/415 |

OTHER PUBLICATIONS

Bard et al. "Electrochemical Methods, Fundamentals and Applications", p. 140, Month Unk. 1980.*
Skoog "Principles of Instrumental Analysis" Third edition, pp. 665, 675–682, Month Unk. 1985.*
Willard et al. "Instrumental Methods of Analysis" Fifth edition, pp. 647, 648, Month Unk. 1980.*

* cited by examiner

Primary Examiner—Robert J. Warden, Sr.
Assistant Examiner—Kaj K. Olsen
(74) Attorney, Agent, or Firm—Burns Doane; Anthony E. Ebert

(57) ABSTRACT

The Applicant's invention comprises an apparatus and method for determining the amount of one or more components in a pulping liquor. At a first electrode, a varying voltage is supplied in a voltage range including the half-wave potential of each component of a liquor to be measured, and accounting for variations in the half-wave potential caused by changing process parameters. At a second electrode, which is roughly $\frac{1}{3}$ to $\frac{1}{4}$ the size of the first electrode, the derivative of current intensity is monitored near the known half-wave potential for the various liquor components. Using curve-fitting means, the derivative of current intensity and selected other process condition data is used to determine concentrations of the various liquor components.

16 Claims, 4 Drawing Sheets

MULTI-ELECTRODE COMPOSITION MEASURING DEVICE AND METHOD

BACKGROUND OF THE INVENTION

1. Field of the Invention

The present invention relates generally to methods of measuring properties of a liquid material having more than one chemical component. More particularly, the present invention describes an apparatus and method for determining the amount of one or more components in a pulping liquor.

2. Description of the Prior Art

The kraft or sulphate process is the most widely used wood pulping process. The process is considered circular since the chemicals used to achieve the desired processing steps are themselves recovered in later steps and reused for further pulping of new raw material. The degree to which each step of the process occurs with the maximum efficiency greatly impacts the purity of the final white liquor as well as the cost of the overall process.

In the kraft process, wood chips are digested to dissolve the lignin that holds the wood fibers together thereby producing clean fibers for further processing into a myriad of paper-based products. The digestion of the wood chips occurs in an alkaline solution mainly consisting of NaOH ("hydroxide") and Na2S ("sulfide"). As the process proceeds, the hydroxide becomes consumed and the sulfide slowly converts to hydroxide and maintains a residual throughout the cook. The resulting pulp fibers are washed and removed leaving a solution, called black liquor, containing the lignin dissolved from the wood chips and the residue hydroxide and sulfide. The black liquor is burned in a boiler leaving a smelt primarily consisting of sulfide and Na2CO3 ("carbonate"). This smelt is dissolved in water or "weak wash liquor" to produce green liquor. The objective of the remaining steps of the process is to convert the carbonate of the green liquor to hydroxide so that the hydroxide can be recycled and reused in the pulping process.

The reaction for converting the carbonate to hydroxide is often referred to as the "causticizing process" or the "causticizing reaction". The causticizing reaction, carried out in a "slaker" and a series of "causticizers", produces a material known as white liquor which ideally has a high degree of hydroxide and only a small amount of carbonate. An inefficient causticizing process results in relatively less hydroxide than ideal and more carbonate than ideal. The causticizing reaction is controlled by the amount of lime introduced to the slaker and the flow rate of green liquor into the slaker. To produce white liquor having the appropriate characteristics, lime must be input to the slaker at the appropriate rate. There are various known approaches for measuring characteristics of the green liquor and/or the white liquor and relating those measurements to the current state of the causticizing reaction. The objective of each of these known methods is to provide an appropriate signal for the control of lime introduction to the slaker. U.S. Pat. No. 4,236,960 issued to Hultman et al. on Dec. 2, 1980 describes one method for controlling the causticizing reaction. A sample stream of green liquor and a sample stream of white liquor are routed to a $CO_2$ analyzer. A single $CO_2$ analyzer is used to make sequential measurements of the liquors or two $CO_2$ analyzers are used, one for each liquor. Each of the sample liquors is mixed with an acid solution so as to acidify the sample and convert carbonate to carbon dioxide gas. The amount of carbon dioxide gas is measured and the $CO_2$ measurement is used as an indicator of the carbonate in the green liquor and in the white liquor. Various calculations are provided whereby the $CO_2$ measurement for each liquor is related to the carbonate level in the liquor. The amount of lime introduced to the slaker is adjusted accordingly. The Hultman method measures only a sample of the liquor. The measurement is relatively complex in that it involves introducing an additional reaction to create a by-product, $CO_2$, that can be measured. The measurement of $CO_2$ is not directly related to the causticizing reaction and is therefore only an inferred measurement.

U.S. Pat. No. 4,536,253 issued to Bertelsen on Aug. 20, 1985 describes another method for controlling the causticizing reaction. Bertelsen teaches that the progress of the causticizing reaction can be measured by making a differential conductivity measurement. The conductivity of the green liquor is measured prior to the slaker and the conductivity of the white liquor is measured after the slaker. Equations are provided whereby the conductivity measurements are related to the progress of the causticizing reaction. The amount of lime introduced into the slaker is adjusted accordingly. White and green liquor are comprised of various components each of which has its own set of characteristics. A measurement of a single characteristic of the entire white or green liquor, as taught by Bertelsen, can result in errors. The major cause of these errors being concurrent changes in two or more components which mask the exact changes of each component separately. For example, green liquor has a small amount of hydroxide which contributes disproportionally to the conductivity measurement of the green liquor since the carbonate component of the green liquor has a relatively low conductivity. Thus, a relatively small variation in the amount of hydroxide in the green liquor results in a disproportionally significant change in the conductivity measurement of the green liquor. The opposite problem occurs on the other side of the causticizing reaction when measuring the conductivity of the white liquor. The Bertelsen method assumes that chemicals other than those of interest to the causticizing reaction are not present or do not vary in the measured liquors. This assumption is rarely true in practice and leads to errors in the Bertelsen measurement. The Bertelsen method also relies on a rigid mathematical formulation based on the conductivity measurements even though there are multiple components of each of the liquors, each of which can vary independently.

A further disadvantage of Bertelsen is that it makes use of a constant excitation voltage, and therefore measures the sum of all ions that react at or below that voltage. This constant voltage system typically also requires the use of a very well defined reference electrode, normally a liquid junction. These precise electrodes typically have a very short lifespan. Constant voltages systems can also be easily disturbed as the analyses temperature or composition changes, because these factors affect the ideal measurement potential.

While at fist glance some types of measurement systems outside the paper industry might seem applicable to improve on the above types of measurements, these systems are typically designed as low current systems, and are incompatible with the highly conductive liquors of the paper industry. Ion specific electrodes, such as Alpha model ISE-8750 sold by Omega Engineering, Inc., can measure Carbonate, but only up to 440 PPM (0.4 grams/liter) Additionally, these electrodes become fouled or poisoned by the sulfur in the liquor. The same is true for pH electrodes, which can sense the hydroxide imbalance in the solution. The pH electrodes become easily poisoned, and are not accurate at the high hydroxide concentrations of white liquor.

Thus, there exists a need for a continuous measurement of active chemicals in the causticizing and re-causticizing processes. There exists a further need for a continuous measurement which provides significant improvement over one that only occurs at periodic intervals, as is the case with sampling or off-line systems. There exists a need for measuring characteristics of individual components of the green liquor and the white liquor during the causticizing and re-causticizing reactions to prevent masking of a change in one liquor component by another. There exists a need for accomplishing the above in the face of changing process parameters, such as pH, temperature, unknown impurities and other factors which influence concentration measurements. There exists a further need to accomplish the above using durable sensor components to reduce process and/or measurement system down time and maintenance costs.

SUMMARY OF THE INVENTION

The Applicant has solved these and other problems by providing a method and apparatus for measuring liquor components, such as those in the green liquor and white liquor which result during a causticizing process. These measurements can be used to achieve more effective control of the causticizing or other (i.e. digestive) reaction for the production of white liquor or other desired output products (e.g., pulp consistency, degree of digestion, etc.). The Applicant's invention further allows measurement of each relevant component of each of the liquors to occur concurrently. These results are achieved in a system that continuously measures the stream of liquor as opposed to sampling the liquor stream, and is effective even in the face of changing process parameters, such as pH, temperature, unknown impurities and other factors which influence concentration measurements. Further, the Applicant's invention allows durable sensor components to be used which would otherwise be non-ideal due to their difficulty in maintaining a stable voltage.

The Applicant's invention comprises the following steps. At a first electrode, a varying voltage is supplied in a voltage range including the half-wave potential of each component of a liquor to be measured, and accounting for variations in the half-wave potential caused by changing process parameters. At a second electrode, which can be roughly ⅓ to ¼ the size of the first electrode, the derivative of current intensity is monitored near the known half-wave potential for the various liquor components. Using look-up tables, iterative curve-fitting means or other methods, the derivative of current intensity and selected other process condition data is used to determine concentrations of the various liquor components.

The electrodes may be composed of platinum or a similar inert material with little worry about conductivity variations of the electrode material. Gold, carbon, graphite, iridium, and palladium are all largely inert and my serve as viable options as well. Other metals such as Stainless steel and titanium are possible within limited voltage ranges.

DETAILED DESCRIPTION

Figure 1:
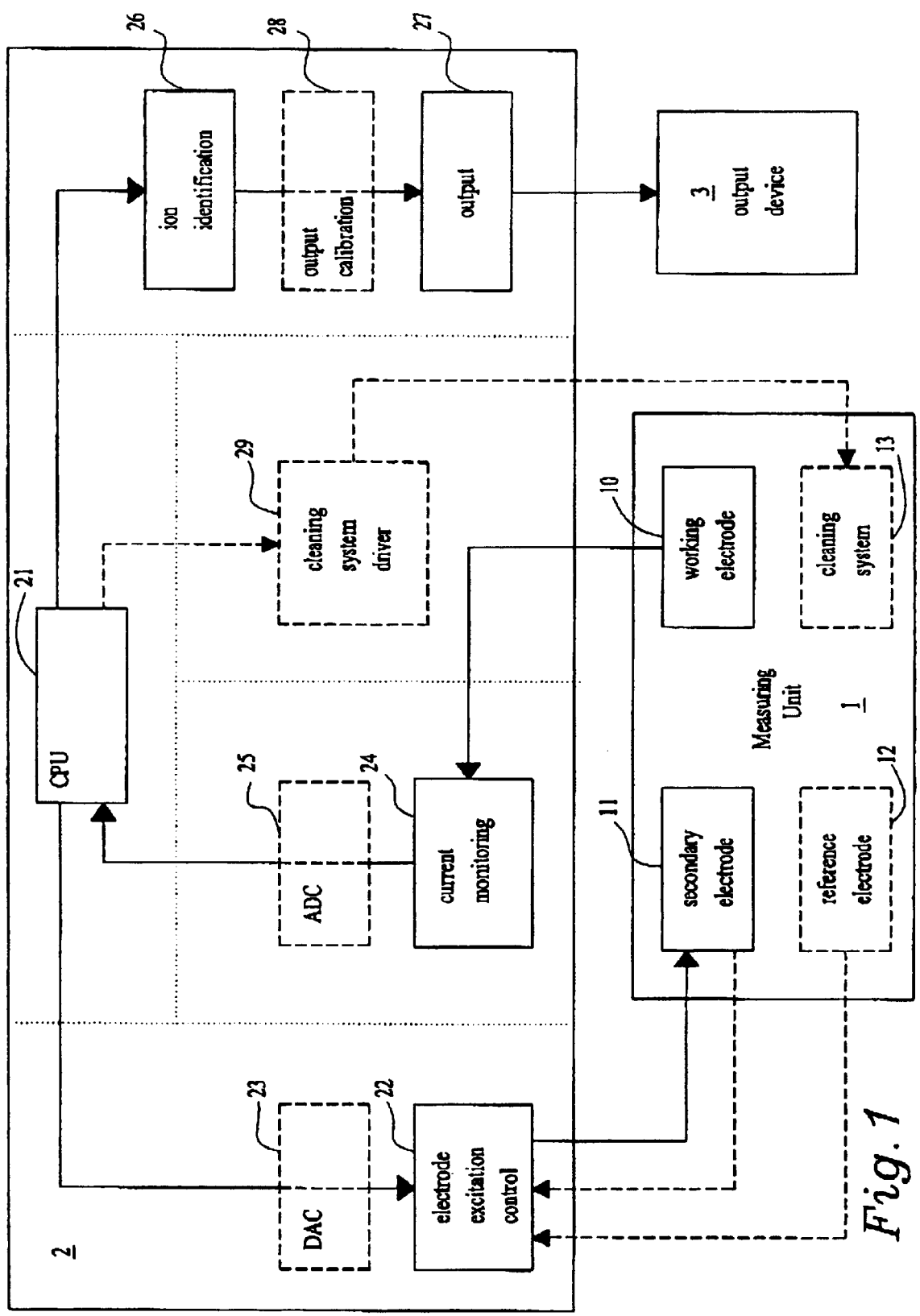
FIG. 1 shows a block diagram of the Applicant's inventive system.

The present invention as described in this application is applied to the measurement of sodium hydroxide, sodium carbonate and sodium sulfate, which occur in various concentrations at a number of stages of the causticizing and re-causticizing process. However, during these processes, other ions may be at work which are useful to monitor with the Applicant's system, particularly since all ions in the liquor effect the overall conductivity. Further, the Applicant's measurement system is useful for digestive process monitoring as well as in other areas inside and outside the pulping industry.

Consequently, exactly when and where various chemicals occur is not relevant to this invention, and therefor, for the sake of brevity, a detailed description of the causticizing process will be omitted. However, the reader is directed to U.S. Pat. No. 5,822,220 to Baines, et al. which includes an outstanding description of one type of causticizing process to which the Applicant's system is applicable.

The measurement technology that is used to determine the relative concentrations of the individual liquor components of the present invention is generally described as a voltametric measurement. The basic concept behind voltametric measurements is the recognition that, for certain chemical components, there is a given voltage range over which the current flowing between electrodes of a measuring device placed in the solution varies from a small level, that is essentially independent of the voltage applied to the solution, up to an intermediary quasi-stable level that varies with the content of the component of interest in the liquor to a very high level that again is essentially independent of the voltage applied to the measuring device.

A voltametric measurement of a given component of a liquor involves obtaining repeated measurements of current-voltage points for voltages within a potential region of interest for that particular component. The various current-voltage measurements form a voltametric-current curve for the given component that can be compared to a similar curve for a solution having a known content of the given component. The comparison will typically provide some information about the content of the specific component.

The Applicant however has recognized that this basic measurement method may be substantially improved upon using several techniques. Primarily, the Applicant has recognized that the ratio of change in current to change in voltage (dI/dv) in and around the half-wave potential is useful in obtaining much more accurate measurement of ion concentrations. The half wave potential is the point where the current is mid-way between the lower level (independent of voltage) and the upper plateau. It is also the point on the curve where the slope is most vertical (again independent of voltage). Furthermore, by examining the dI/dv curve, rather than simply the current intensity, process changes which otherwise disturb ion concentrations measurements in older voltametric systems, are automatically compensated for.

In terms of present-day hardware, a block diagram of a system incorporating the Applicant's new voltametric measurement system is shown in FIG. 1. In the Figure, large blocks 1 and 2 represent a measuring unit and computing unit, respectively. Output from the computing unit will be fed to an output device, labeled 3 in FIG. 1, such as a control system for making causticizer control changes, and/or a display device for showing the results of the measuring unit to a user.

Measuring unit 1 comprises at least a first or working electrode 10 and a secondary or second electrode 11. Measuring unit 1 may also contain other components. Particularly, a reference electrode 12 is added in one possible embodiment, described in detail below. The measuring unit may also contain a cleaning system 13 used to help maintain electrode accuracy, and reduce electrode wear.

Within the computing unit, a CPU 21, microcontroller, microprocessor, grouping of several of these devices, or other logic unit controls operation of the measurement system. As herein described, the measurement system converts analog data from the electrodes to digital data for processing. While this is a preferred arrangement, use of an analog or other type of control system would also be possible. In any event, CPU 21 plays three essential roles in the measurement system. First, it provides excitation control signals to an electrode excitation control circuit 22. Depending on the type of electrode excitation control, this may occur directly, or via a digital to analog converter (DAC) 23. Electrode excitation control circuit 22, in turn drives the voltage on secondary electrode 11 in the measuring unit.

The second role of CPU 21 is to control a current monitoring circuit 24 which monitors current flow (i.e. magnitude and/or gradients) from working electrode 10 in measuring unit 1. Typically, the communication between CPU 21 and the current monitoring circuit 24 will occur via an analog to digital converter (ADC) 25 which converts the analog current values from working electrode 10 to digital values useful to CPU 21. Device 24 may be called and will be referred to as a current sensing device. As the Applicant will explain shortly, the key measurement needed is the derivative of current passing through working electrode. The measurement made by the current monitoring circuit may actually be current, and CPU 21 may create the derivative value. In any event, the actual location where the derivative is calculated is not critical, except to note that any manipulation of the data created by current monitoring circuit should preserve derivative of current data, if this data is not collected directly.

The last role of CPU 21 is operation of an ion identification circuit 26 which takes data from the CPU regarding current, and current gradients (i.e derivative), to determine liquor ion concentrations. This data is thereafter passed to an output circuit 27 which provides control signals to one or more output devices 3 for control, storage and/or display of measurement-related data. Some form of output calibration circuit 28 may be included between ion identification circuit 26 and output circuit 27. For example, this circuit may be used to adjusts output values based on periodic, continuous or initial calibration data.

While the Applicant has described various system elements as circuits, it is understood that these elements may actually be implemented in software instead of physical circuits. This choice of implementation would not effect the applicability of the Applicant's invention.

If some form of cleaning system 13 is employed either as part of or separate from measuring unit 1, the CPU may also be used to operate a cleaning system driver circuit 29, which controls an ultrasonic, mechanical, chemical or other type of cleaning system. As is usually implemented, CPU 21 will periodically initiate a cleaning cycle by triggering electrically actuated relays. These send power to cleaning system 13, and cause the cleaning system to clean the electrodes. The need and frequency for cleaning will depend on many factors, such as electrode composition, how quickly the particular liquors foul the electrodes and other factors. During cleaning, CPU 21 will usually ignore the measurements taken, preventing erroneous output values which can be generated during a cleaning cycle.

Figure 2:
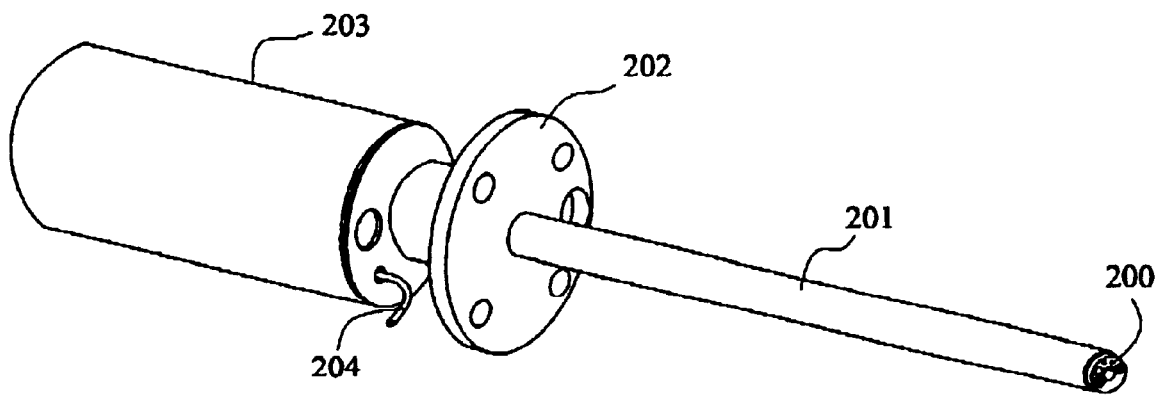
FIG. 2 and FIG. 3 show one possible physical configuration of the Applicant's inventive system.
Figure 3:
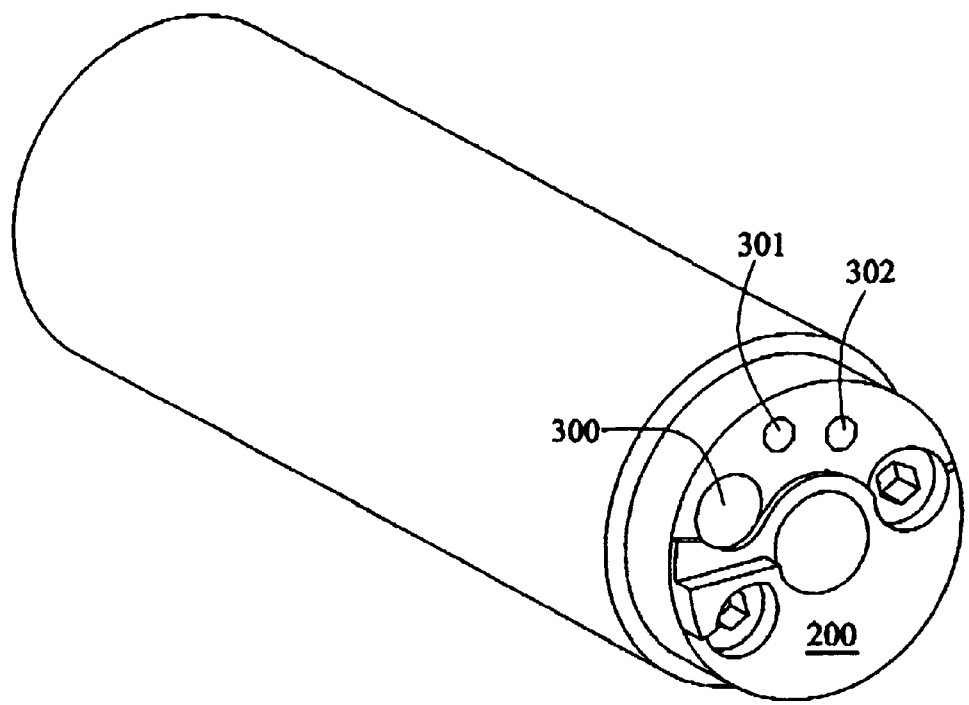

Prior to description of the operation of the Applicant's measurement system, description of one possible physical configuration of measuring unit 2 is provided, with reference to FIG. 2 and FIG. 3. The measuring unit may be mounted in any number of locations throughout the pulping process, within a liquid stream. Typically, these locations will at least provide a measure of the green liquor input to the causticizer, and white liquor in or after the causticizer. The reader may conceive of other locations of particular interest, although location of the Applicant's system is not critical to its operation, or even that it be used to measure causticizing liquids. FIG. 2 shows the entire measuring unit, including probe tip 200, probe tip assembly 201, mounting bracket 202, and rear assembly 203. Probe tip assembly 201 locates probe tip 200 a short distance into the process vessel, in contact with the liquid to be measured, and shelters wires going from probe tip 200 to housing assembly 202. Rear assembly 203 will typically contain the cleaning system mechanics, cleaning solvent supply etc. Rear assembly 203 also routes wires 204 from probe tip 200 to computing unit 2. FIG. 3 shows a close-up view of probe tip 200. In the embodiment shown, one larger electrode 300, and two smaller electrodes 301 and 302 lie in a common surface of the probe tip. The larger electrode is used as secondary electrode 11 and may be three to four times the size of the remaining two electrodes. This physical configuration ensures that working electrode 10, and not secondary electrode 11, limits current flow through the measurement system. Further, keeping working electrode 10 small reduces the energy required to excite the measured liquor and produce a measurement. The small size of the working electrode also reduces the amount of current required to operate the measurement system, minimizing errors caused by solution and wiring resistance.

If reference electrode 12 is implemented, it is located as close as practical to working electrode 10. Further, while not crucial, the three electrodes should be mounted in the same plane. This configuration best defines the current path between the electrodes, and eliminates errors that could otherwise be caused by streaming flows in other configurations.

The electrodes may be made of platinum, or another inert conductive material, such as gold, graphite, iridium, palladium or carbon. Other metals such as Stainless steel and titanium are possible within limited voltage ranges. The probe tip itself is typically made of PEEK, ceramic or other non-conductive material. The probe tip assembly is usually composed of a Stainless Steel or other material having chemical resistance.

Detailed description of the operation of the Applicant's invention is now provided with reference to FIG. 1. As part of the background operation of the measurement system, CPU 21 varies the setting on DAC 22 over time, causing the DAC to create a varying voltage output on secondary electrode 22. In general the voltage is varied over one or several ranges around the half-wave potential of the ions desired to measured. The ions measured are typically sodium hydroxide, sodium carbonate and sodium sulfide. For example, a voltage ramp from 0 to 1.3 volts may be appropriate for a measurement system utilizing separate reference electrode 12. A voltage sweep of −1.3 to 2.5 volts may be more appropriate for a measurement system which does not use a reference electrode. The range and characteristics of the voltage sweep (e.g. speed, shape of the voltage waveform) is adjusted further based on several types of criteria. First, the voltage is adjusted relative to reference electrode 12. This adjustment accounts for changes in the conductivity of the liquid being measured. Second, the range of the voltage may be adjusted based on external signals into the CPU, such as temperature or other process parameters which have an effect on the ideal voltage range in which the measurement system measures. For example, process conditions may shift the location of a particular half-wave potential from its location during calibration of the system to another location. External data to the CPU may also select a different set of liquor components to measure. Thirdly, the voltage range can be adjusted based on previous collected data, or empirically identified or calculated measurement locations. Details on identification of identified measurement locations will be described shortly.

The Applicant also notes that a plurality of voltage sweeps or some other voltage wave shape may be more useful for the reader's chosen application or system conditions. For example, less data (a faster sweep) away from the identified measurement locations and more data near the measurement location would allow faster control (since new data would occur more often). As a second example, skipping known areas containing no new ion activity would also allow increased measurement, and thus control speed.

As the voltage on secondary electrode 11 is altered, it triggers ADC 25 to collect data about current flow into or out of current monitoring circuit 24, which monitors the current flowing through working electrode 10.

Data is collected for one cycle of the voltage profile. For example, the Applicant has used a system taking 512 measurements at different voltages during a 5 second cycle. The collected data is stored in computing unit 2 or elsewhere for further processing, and the cycle repeats. Prior to initiation of the next cycle, adjustments can be made to the voltage profile to improve measurement output.

The data collected from ADC 25 is thereafter assembled into one or more waveforms, and this data is applied to ion identification circuit 26 of computing unit 2. The ion identification circuit identifies points in the waveform where increased ionic activity occur. Particularly, the ion identification algorithm searches through the waveform and identifies the places where the dI to dV ratio changes dramatically. In a particularly preferred embodiment, the algorithm then locates the precise point where the maximum dI/dv occurs.

As indicated, the approximate location of each reaction of interest is already known; these values, called half wave potentials, are well documented for various ions. By defining the search area to cover only the normal potential ranges of the ions of interest, the system can selectively detect any ion in the solution being measured.

At each point where an ion has been identified, the rate of current change is recorded, as well as other information including for example, the amount of current flow, and the voltage at which the ion's reaction was located.

Since changing dI/dV ratios are being measured, and not current magnitude, there is no need for a high precision reference electrode (such as a liquid junction). Low precision electrodes, such as suggested by the applicant, may disturb absolute current magnitude values, and would by inappropriate for many prior art systems. Measuring the ratio rather than the absolute magnitude of current also allows the Applicant's system to be used even in the face of temperature, solution pH, conductivity, flow and other parameter changes which alter the half-wave potential of the ions being measured.

Figure 4:
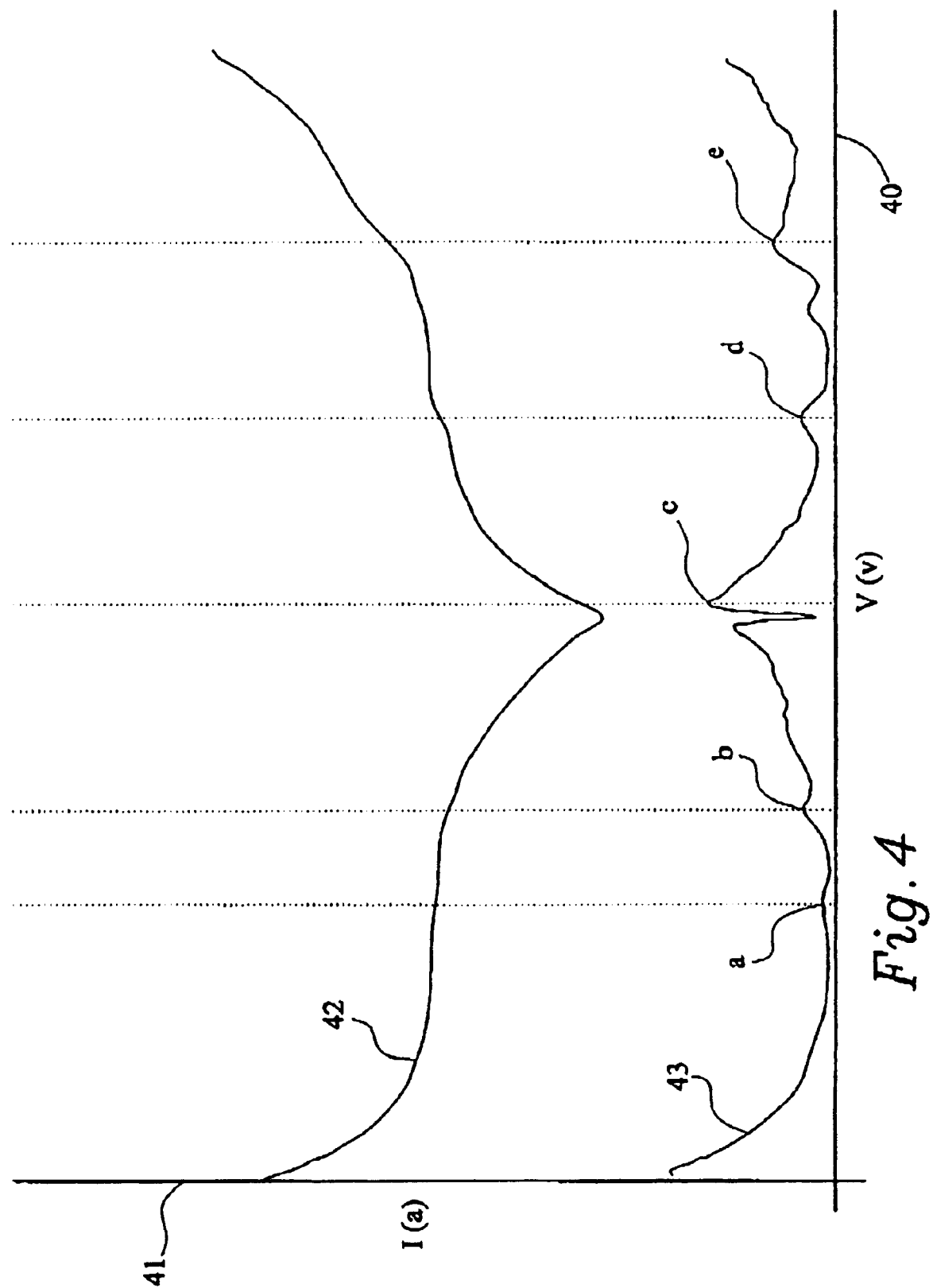
FIG. 4 shows a current and derivative of current graph upon which the Applicant's ion identification circuit identifies ion activity locations and magnitude.

In any event, FIG. 4 shows a graph of lab data for a pulp causticizing liquor. In the graph, x-axis 40 represents voltage and y-axis 41 is scaled in amperes and the unitless value dI/dV. Upper graph 42 shows the voltage on the secondary electrode. The graph includes two voltage sweep cycles. Lower graph 43 represents the derivative of the upper graph (i.e dI/dV). The derivative graph clearly shows a number of peaks, marked a–e, in current gradient. Each peak represents a separate ion reaction. Numerous mathematical methods are available, as the reader is aware, for automatically identifying these peaks. For example, monitoring the dI/dV graph for a set of low-high-low values in a pre-selected small range would quickly identify each ion peak.

To improve system operation, the location of each peak may be fed back into the electrode excitation circuit 22, adjusting for higher or lower ion half-wave potentials than expected. Constant or periodic adjustment of the sweep ranges can speed up data production and measurement speed, since the ranges are typically made wider only to prevent missing an ion half-wave potential peak. Smaller ranges can therefore be used if the half-wave potentials are carefully monitored with this feedback technique.

In the main part of the process the data thus compiled, as well as possibly some external data, is applied to a linear equation obtained through an initial calibration or other means. Several calibrations can be stored and generated concurrently, allowing the system to output the concentration of several different chemical components in the solution being measured. The calculated values from the linear equation may then be sent to output circuit 27, which converts the algorithmic result to an output device-compatible output. For example, the algorithm's output can be converted to a 4 to 20 ma standard industrial output value. This output signal can then be used by a control system or the data may be displayed on a recorder, CRT, or other output device, such as shown in FIG. 1 at numeral 3. Transport of the data may be by any available means, such as a serial connection, a network connection or Fieldbus or other means.

Several possible calibration options are available for correlating current data to actual liquor component concentration values. While it is possible to calculate concentrations based on known properties of the ion and the current flowing, the Applicants have utilized a calibration method which makes use of linear regression and lab liquor samples having known component concentrations to produce a set of calibration coefficients. In the simplest case, dI/dv or a combination of dI/dv and I at a particular voltage (i.e. a half-wave potential for a particular ion), is associated with a particular concentration. In this type of system, conductivity caused by ions at lower voltages are subtracted from the measurement prior to producing a result. This is possible since a simple voltage sweep should show how each ion contributes to overall conductivity.

Other systems may add in other factors such as temperature, liquor pH, or derivative values at other voltages (such as at the half-wave potential of other ions). In the Applicant's more complicated, albeit more accurate method, a series of equations may be created:

$$S_1(1)X_1+S_2(1)X_2+S_m(1)X_m+\ldots+X_0=L(1) \quad (1\text{-}1)$$

$$S_1(2)X_1+S_2(2)X_2+S_m(2)X_m+\ldots+X_0=L(2) \quad (1\text{-}2)$$

$$S_1(n)X_1+S_2(n)X_2+S_m(n)X_m+\ldots+X_0=L(n) \quad (1\text{-}3)$$

$$S_1(N)X_1+S_2(N)X_2+S_m(N)X_m+\ldots+X_0=L(N), \quad (1\text{-}4)$$

to describe the state of the system under various process conditions. In the above equations, L(n) represents laboratory analyzed liquor sample values for the equation process conditions (i.e. the actual values for the desired measured parameters at the give time). $S_1(1) \ldots S_m(N)$ represent various output signals such as one or more current derivatives, one or more current values, their associated secondary electrode voltage, temperature, or other measured parameters. The value n represents the selected functions at a specific time. The set of equations chosen may represent all possible equations with the selected set of output signals, or may be some subset of these based on a designer's understanding of the more critical signals. The weights $X_m$ are solved using matrix algebra/linear regression. The algorithm uses the "sum of squares" method to minimize the sum of error through all equations.

Since there will likely be no set of coefficients that exactly fits all equations simultaneously, a coefficient of correlation, R, is also output which represents how well the linear model fits the test data. Basically, R is calculated by the ratio of standard deviations of the lab data and calculated data, where 1.0 means that all the variation in lab data can be explained by the variations in the measured signals, and 0 means that there is no relationship between the lab data and measured signals. The coefficient of correlation is used to select which system parameters, of the ones chosen, provide the most accurate representation of the system. The reader may be aware of other correlation methods equally as applicable.

With calibration completed, the system can generate real-time output values by using the output calculation formula:

$$O = S_1 K_1 + S_2 K_2 + S_3 K_3 + S_4 K_4 + \ldots S_m K_{m+} \ldots + K_0, \quad (1\text{-}5)$$

where $S_m$ represents selected signals representing system parameters (selected using R, for example), and $K_m$, weighting coefficients generated by the just described calibration algorithm. $k_0$ represents an offset or zero-intercept constant.

If more than one ion type is being monitored, this same process would be repeated for each ion type. One such equation would be created for each liquor component to be measured.

The Applicant contemplate that a second or higher order polynomial equation may be preferable under some process conditions. If this is the case, the equations would be solved to produce polynomial coefficients, rather than liner ones.

The calibration algorithm can also be incorporated into the measuring system's processor, so that the system becomes self-calibrating. In one possible implementation, the system would accept input from the user, indicating the results of actual tests taken. The system could then accumulate these vales in it's internal memory, and match them up, based on time stamp, with it's own outputs at that time. When differences are identified by the calibration algorithm, the measuring system re-runs the linear regression function, and if the R value is significantly higher, it will alter it's calibration coefficients. Such a system could, for example, adapt for drift due to aging of the electrodes or other components, or other sources of error.

As the Applicant has indicated, it is possible to implement the Applicant's invention using only two electrodes, eliminating the separate reference electrode. The reference electrode in a typical three electrode system is used to establish the base or zero potential point against which the other electrodes are measured. Using the ion identification circuit, it is no longer necessary to have a precise reference electrode. By further extension, it is possible to create a system where the reference and secondary electrode are the same; thus obtaining the same measurement with only two electrodes.

To accomplish this, instead of using the zero from an external reference (i.e. a separate reference electrode), the zero point is defined to be the voltage at which no current flows into or out of the working electrode. All potentials are then referred to against this point.

Since the Applicant's invention measures ionic activity, the voltage locations for each ion can be expressed in relative terms. Rather than measuring an ion at +100 mV relative to a zero reference, for example, if the secondary electrode serves as the reference electrode, this ion may react at close to +200 mV from the rest potential of the secondary electrode. With the reference electrode eliminated, the reaction potential will change as a function of conductivity in the solution being measured. The potential of the secondary electrode will necessarily be greater than the potential of the solution immediately adjacent to the working electrode. Therefore, for this embodiment of the Applicant's invention to operate properly requires that the voltage on the secondary electrode be swept though a much greater range of voltages to ensure that the ion's potential is covered. Where typically a 0–1250 mV range would be appropriate with a reference electrode, −1250 mV to +2500 mV would be needed using a two electrode system, and may have to be further expanded if the conductivity is expected to vary widely.

Further, when ramping to high voltages (i.e >1200 mV), it is further necessary to include a current limiting device at the secondary electrode. The current limiter will prevent excessive voltage from causing over-potential of the electrode, which otherwise would lead to production of hydrogen and oxygen from water in the liquor. This undesirable added reaction would provide a substantial current flow through the working electrode, and would cause electrically generated corrosion even on the typically inert electrodes.

The current limit circuit is accomplished by monitoring the derivative of the current flow, and triggering the limiting device when the derivative of current exceeds a pre-defined value. This value can be calculated based on electrode surface area, and conductivity of the solution being measured, or may be determined empirically.

Figure 5:
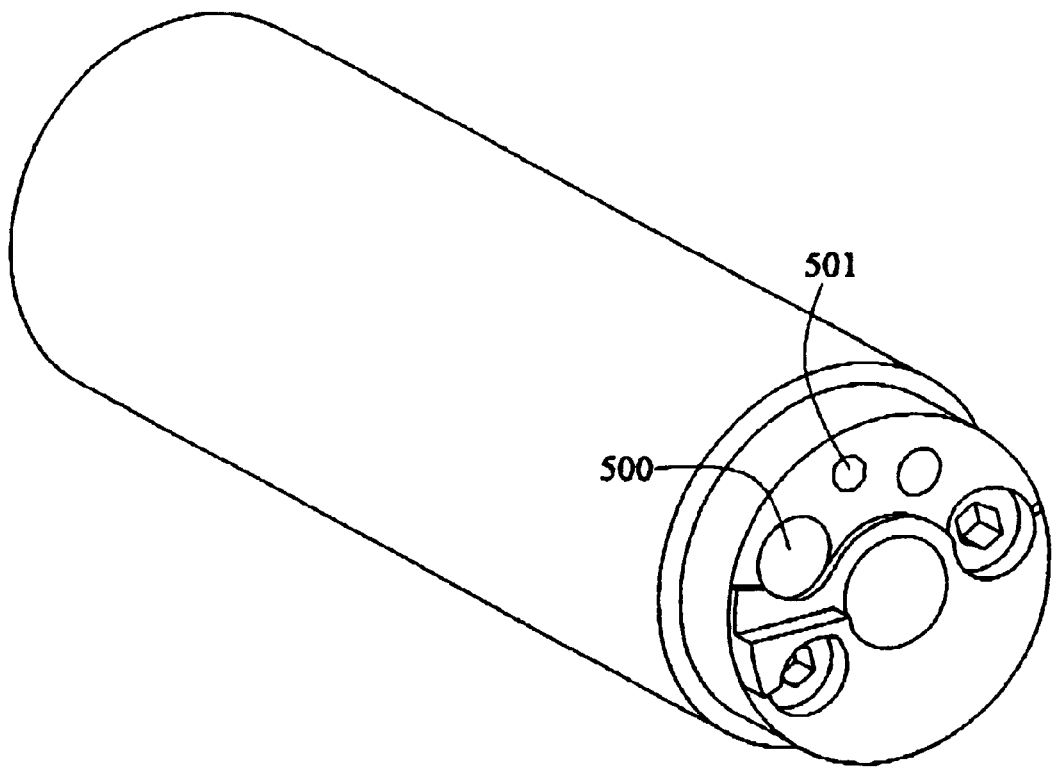
FIG. 5 shows a second possible physical configuration of the Applicant's invention, utilizing the secondary electrode as the reference electrode.

FIG. 5 shows the applicants new probe tip making use of only two electrodes, rather than three. In the Figure, secondary/reference electrode 500, is shown ⅓ to ¼ larger than working electrode 501. The third electrode is shown capped off in the figure, but may also be eliminated entirely.

Thus since the invention disclosed herein may be embodied in other specific forms without departing from the spirit or general characteristics thereof, some of which forms have been indicated, the embodiments described herein are to be considered in all respects illustrative and not restrictive. For example, while the Applicant's invention has be shown and described in terms of the causticizer, it could easily be applied to the digester to measure Sodium Sulfide ($Na_2S$) and Sodium Hydroxide (NaOH), or the industry standard EA (Effective Alkali, which is NaOH+½$Na_2S$) The scope of the invention is to be indicated by the appended claims, rather than by the foregoing description, and all changes which come within the meaning and range of equivalency of the claims are intended to be embraced therein.

The embodiments of the invention in which an exclusive property or right is claimed are defined as follows:

1. An apparatus for identifying the amount of one or more components in a liquid, comprising:
   a controller operative to supply current in a prescribed voltage range, the voltage range being determined based upon an expected location of half-wave potentials for selected components to be detected;

a secondary electrode in electrical communication with the controller and operative to supply current in the prescribed voltage range;

a working electrode receiving current from said secondary electrode;

a current sensing device operative to detect the current intensity of said working electrode; and calculating means in electrical communication with the current sensing device and the controller, the calculating means being operative to determine the derivative of current intensity versus voltage relative to a reference potential and determine the concentrations of one or more components in the liquid by identifying peaks in the derivative of current in expected locations of the half-wave potentials for the components to be detected, the calculating means being configured to adjust the prescribed voltage range of the controller in response to process parameters and the location of the peaks identified in order to facilitate quicker identification of the components.

2. The apparatus of claim 1 further comprising a reference electrode, which provides the reference potential for said working electrode.

3. The apparatus of claim 1 wherein said secondary electrode provides the reference potential for said working electrode.

4. The apparatus of claim 1 wherein the preselected profile comprises sweeping the predetermined voltage on the secondary electrode through a single voltage range containing the half-wave potential of each ion to be measured.

5. The apparatus of claim 1 wherein the one or more voltage ranges cover the half-wave potential of every component in the liquid sought to the measured.

6. The apparatus of claim 1 wherein one or more of the electrodes are comprised of platinum.

7. The apparatus of claim 1 wherein one or more of the electrodes contains one of the following metals: gold, carbon, graphite, iridium, palladium, stainless steel and titanium.

8. The apparatus of claim 1 wherein the secondary electrode is larger than the working electrode.

9. The apparatus of claim 8 wherein all electrodes lie in a common plane.

10. A method of measuring the concentration of one or more components in a liquid, the method comprising the steps of:

producing a current flow at a voltage within a prescribed range at a first location in the liquid;

measuring the current flow in the liquid at a second location;

determining a derivative of the current flow versus voltage relative to a reference potential;

determining the concentration of the one or more liquid components by identifying peaks of the derivative of current flow versus voltage; and adjusting the voltage within the prescribed range at the first location in response to process parameters and the peaks identified in order to facilitate quicker identification of the components.

11. The method of claim 10 further comprising the step of maintaining the voltage at the second location relative to a third location.

12. The method of claim 10 further comprising the step of maintaining the voltage at the second location relative to a first location.

13. The method of claim 10 wherein the measuring system is initially calibrating the following steps:

selecting a set of process conditions which effect the concentration of a component of the liquid to be measured;

creating a set of equations representing addition of current change and one or more of the selected set of process conditions, each process condition thereafter associated with an unknown weighting coefficient;

determining a lab value for each equation in the set;

performing linear regression to solve for the unknown weighting coefficient; and creating one or more working equations using the solved-for weighting coefficients which are thereafter used to determine concentration of the one or more liquid components.

14. The method of claim 13 wherein the coefficient of correlation, R, is used to select which of the set of equations of selected process conditions is used to create the one or more working equations.

15. The method of claim 13 wherein the set of equations of selected process conditions represent all possible permutations of the selected set of current change and the one or more of the selected set of process conditions.

16. The method of claim 13 wherein the set of equations include at least current, derivative of current and the half-wave potential for the liquor component being measured.

* * * * *